United States Patent [19]

Sachinvala et al.

[11] Patent Number: 5,302,676
[45] Date of Patent: Apr. 12, 1994

[54] POLYMERS HAVING ENHANCED CROSSLINKING EFFICIENCIES, AND METHODS FOR THEIR PREPARATION USING 1',6,6'-TRIMETHACRYLOYL-2,3,3',4,4'-PENTA-O-METHYL SUCROSE AS A CROSSLINKING AGENT

[75] Inventors: Navzer D. Sachinvala; Reui F. Ju, both of Aiea, Hi.; Morton H. Litt, Cleveland, Ohio

[73] Assignee: Hawaiian Sugar Planters' Association, Aiea, Hi.

[21] Appl. No.: 91,283

[22] Filed: Jul. 15, 1993

Related U.S. Application Data

[60] Division of Ser. No. 877,813, May 4, 1992, Pat. No. 5,248,747, which is a continuation-in-part of Ser. No. 697,983, May 10, 1991, Pat. No. 5,116,961, which is a continuation-in-part of Ser. No. 623,548, Dec. 7, 1990, abandoned.

[51] Int. Cl.$^5$ ............... C08F 218/14; C08F 226/02; C08F 220/10
[52] U.S. Cl. .................. 526/238.23; 526/307.2; 526/328.5
[58] Field of Search .......... 526/238.23, 307.2, 328.5

[56] References Cited

FOREIGN PATENT DOCUMENTS 58-114013  7/1983  Japan .

*Primary Examiner*—Joseph L. Schofer
*Assistant Examiner*—Wu C. Cheng
*Attorney, Agent, or Firm*—Burns, Doane, Swecker & Mathis

[57] ABSTRACT

The invention relates to crosslinked polymers and methods for making crosslinked polymers using 1',6,6'-trimethacryloyl-2,3,3',4,4'-penta-O-methylsucrose as a novel crosslinking agent. The invention is particularly suitable for crosslinked polymers containing methacrylate ester, acrylate ester or acrylamide monomers.

10 Claims, No Drawings

POLYMERS HAVING ENHANCED CROSSLINKING EFFICIENCIES, AND METHODS FOR THEIR PREPARATION USING 1',6,6'-TRIMETHACRYLOYL-2,3,3',4,4'-PENTA-O-METHYL SUCROSE AS A CROSSLINKING AGENT

RELATED APPLICATIONS

This application is a divisional, of Application Ser. No. 07/877,813, filed May 4, 1992 now U.S. Pat. No. 248,747. Which is a continuation-in-part of U.S. application Ser. No. 07/697,983, filed May 10, 1991, now U.S. Pat. No. 5,116,961, which is a continuation-in-part of U.S. application Ser. No. 07/623,548, filed Dec. 7, 1990, now abandoned.

FIELD OF THE INVENTION

The subject invention relates to polymerizable mixtures suitable for the production of polymers having enhanced crosslinking efficiencies, methods for producing such polymers and the resulting polymers.

BACKGROUND OF THE INVENTION

The use of crosslinking agents in the synthesis of polymers is known in the art. For example, compounds such as glycerol, sorbitol, 3,5-dihydroxy-methylbenzyl alcohol and pentaerythritol find wide applicability as polyfunctional crosslinking agents.

A crosslinking agent which is commonly used is 2-ethyl-2-hydroxymethyl-1,3-propanediol or trimethylolpropanetriol. This crosslinking agent, or trifunctional crosslinking agents as it may be more accurately described is used in particular to produce crosslinked polyesters.

It has additionally been known to functionalize trimethylolpropanetriol further to produce other trifunctional crosslinking agents. For example, it is known to treat 2-ethyl-2-hydroxymethyl-1,3-propanediol with acryloyl or methacryloyl chloride to produce 2-ethyl-2-hydroxymethyl-1,3-propanediol triacrylate and 2-ethyl-2-hydroxymethyl-1,3-propanediol trimethacrylate. The resulting polyfunctional crosslinking agents find particular applicability in crosslinking reactions with acrylates and methacrylates.

In such methods, the trimethylolpropane triacrylate or TMPTA and trimethylolpropane trimethacrylate or TMPTMA are then reacted with acrylate and methacrylate monomers, preferably in the presence of a sufficient amount of free radical initiator to facilitate polymerization. Such methods are often used to produce crosslinked thermoset polymers. The resultant thermoset polymers find applicability, e.g., in making automobile coatings and composites. Additionally, crosslinked thermoset polymers are used in bulk or thermoset monomers may be diluted with other monomers to produce adhesives or composite materials.

Although both TMPTA and TMPTMA are conventionally utilized as crosslinking agents with both acrylate and methacrylate monomers; there are inherent disadvantages associated with the use thereof. In particular, due to the size of TMPTA or TMPTMA and the symmetry of these molecules, only a small separation exists between the reactive ends of the acryloyl or methacryloyl moieties. Because of this close proximity, these reactive termini may react with themselves in addition to reacting with other acrylate or methacrylate monomers in the polymerizing melieu. The former produces cyclic structures (10 membered rings) and is undesirable since it wastes the double bonds of the crosslinking agent. The latter reduces the overall efficiency of the crosslinking agent. Additionally, internal cyclization often results in a weakened polymeric network which is undesirable if the crosslinked polymer is to be industrially useful.

In order to minimize the recognized problems associated with such crosslinking agents, it had been contemplated in the art to increase the overall concentration of the crosslinking agent in the polymerization mixture as a means of enhancing the degree of crosslinking. However, even at high crosslinking agent concentrations, the resultant polymers may be brittle and mechanically weak. Additionally, the increased concentration of the crosslinking agent renders the polymers undesirably expensive to produce. For instance, it is described, e.g., in Matsumoto et al, "Gelation in the copolymerization of methyl methacrylate with trimethylolpropane trimethacrylate."; *Eur. Polym. J.*, Vol. 25 (4), pp. 385–389 (1989), that the crosslinking efficiency of trimethylolpropane trimethacrylate is only 18% and that 82% of the polymer mixture had internally cyclized despite the fact that an excess of methyl methacrylate was present in the polymerization mixture.

Furthermore, K. Dusek in *Developments in Polymerization-3*, R. N. Howard (editor), Applied Science Publishers, Ltd., London, p. 63, (1982), describes that when methylene bis-acrylamide is used to crosslink polyacrylamide hydrogels at a 10–20% acrylamide crosslinker concentration crosslinking efficiencies are only 10–20%. Such low crosslinking efficiencies may result in polymers which are not structurally load bearing.

Thus, given the described state of the prior art, it is clear that improved methods for producing crosslinked polymers, and improved crosslinked polymers resulting from these methods would be highly desirable.

OBJECTS AND SUMMARY OF THE INVENTION

It is an object of this invention to avoid or alleviate the problems of the prior art.

It is also an object of the invention to provide improved methods for producing crosslinked polymers using 1',6,6'-trimethacryloyl-2,3,3',4,4'-penta-O-methylsucrose as a crosslinking agent.

It is a further object of the invention to provide improved methods for producing crosslinked polymers comprising arcylate ester, methacrylate ester or acrylamide monomers using 1',6,6'-trimethacryloyl-2,3,3',4,4'-penta-O-methylsucrose as a crosslinking agent.

It is another object of the invention to provide improved crosslinked polymers using 1',6,6'-trimethacryloyl-2,3,3',4,4'-penta-O-methylsucrose as a crosslinking agent.

It is still another object of the invention to provide improved crosslinked polymers comprising acrylate ester, methacrylate ester or acrylamide monomers using 1',6,6'-trimethacryloyl-2,3,3',4,4'-penta-O-methylsucrose as a crosslinking agent.

It is another object of the invention to provide polymerizable mixtures which upon polymerization result in crosslinked polymers having enhanced crosslinking efficiencies; which mixtures contain 1',6,6'-trimethacryloyl-2,3,3',4,4'-penta-O-methylsucrose, a monomer which reacts therewith, and optionally a free radical initiator in amounts sufficient to facilitate polymerization.

Finally, it is an object of the invention to provide polymerizable mixtures which upon polymerization result in crosslinked polymers containing methacrylate ester, acrylate ester or acrylamide monomers having enhanced crosslinking efficiencies; which mixtures comprise 1',6,6'-trimethacryloyl-2,3,3',4,4'-penta-O-methylsucrose, a methacrylate ester, acrylate ester or acrylamide monomer and optionally a free radical initiator in relative amounts sufficient to facilitate polymerization and the production of polymers having improved crosslinking efficiencies.

The present inventors have surprisingly discovered that 1',6,6'-trimethacryloyl-2,3,3',4,4'-penta-O-methylsucrose has a very high crosslinking efficiency as compared to conventional crosslinking agents. It has further been discovered that when 1',6,6'-trimethacryloyl-2,3,3',4,4'-penta-O-methylsucrose is used as a crosslinking agent with methacrylate ester, acrylate ester or acrylamide monomers, that there are obtained crosslinked polymers exhibiting enhanced crosslinking efficiencies. Given these enhanced crosslinking efficiencies, crosslinked polymers produced using this crosslinking agent should exhibit enhanced mechanical stability relative to crosslinked polymers produced using conventional crosslinking agents.

It is believed by the present inventors that the high crosslinking efficiencies obtained using 1',6,6'-trimethacryloyl-2,3,3',4,4'-penta-O-methylsucrose as a crosslinking agent are attributable to the large separation (in terms of the number of atoms) between any two methacryloyl moieties. However, the present inventors do not want to restrict themselves to this belief. In the 1',6,6'-trimethacryloyl-2,3,3',4,4'-penta-O-methylsucrose molecule, the distance between the reactive sites of the 6 and 6' methacryloyl moieties is 16 atoms, the distance between the reactive ends at the 1' and 6' positions is 12 atoms and also these two positions are anti in orientation with respect to each other on the fructopyranosyl moiety, the distance between the reactive ends at the 1' and 6 positions is 14 atoms and there is an intervening 2,3,4'-tri-O-methylglucopyranosyl moiety.

Therefore, given the above-described structure of the compound, the possibility of intramolecular cyclization of methacryloyl moieties is highly remote provided an excess of acrylamide or methacrylamide monomers are present in the polymerizable mixture. Thus, 1',6,6'-trimethacryloyl-2,3,3',4,4'-penta-O-methylsucrose should crosslink with various monomers, including in particular methacrylate ester, acrylate ester and acrylamide monomers at relatively high crosslinking efficiencies to form a highly efficient polymeric network.

This is in contrast to conventional crosslinking agents known in the art which contain functional groups which are very closely spaced. This ofen leads to undesirable reactions of a functional group on the crosslinking agent with another functional group on the same molecule. Such a reaction gives rise to a cyclic structure rather than facilitating the formation of an efficient polymeric network. Consequently, this cyclization wastes double bonds and reduces the overall efficiency of the crosslinking agent, and moreover, weakens the internal network of the resultant polymer.

Therefore, the use of 1',6,6'-trimethacryloyl-2,3,3',4,4'-penta-O-methylsucrose should result in improved methods of crosslinking monomers, in particular, acrylate esters, methacrylate esters and acrylamide monomers, and should also result in crosslinked polymers having enhanced crosslinking efficiencies.

DETAILED DESCRIPTION OF THE PREFERRED EMBODIMENTS OF THE INVENTION

As discussed above, the subject invention relates to methods of using 1',6,6'-trimethacryloyl-2,3,3',4,4'-penta-O-methylsucrose as a novel crosslinking agent in polymerization processes, and crosslinked polymers having enhanced crosslinking efficiencies obtained using this crosslinking agent. This crosslinking agent comprises the following structure:

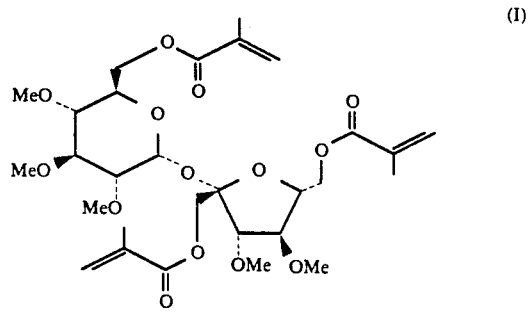

This crosslinking agent may be synthesized by the method which is described in applicants' commonly assigned application, Ser. No. 07/697,983, filed on May 10, 1991, and now allowed. This application and in particular the specific disclosure pertaining to the synthesis of 1',6,6'-trimethacryloyl-2,3,3',4,4'-penta-O-methylsucrose is hereby incorporated by reference in its entirety.

This crosslinking agent will comprise particular applicability for crosslinking acrylate esters, methacrylate esters and acrylamide monomers. However, 1',6,6'-trimethacryloyl-2,3,3',4,4'-penta-O-methylsucrose should also be suitable for crosslinking a variety of monomers which are well known and available in the art.

For example, suitable monomers in the present invention may include methyl acrylate, acrylic acid, methacrylic acid, methyl methacrylate, hydroxyethyl methacrylate, ethyl vinyl ether, styrene, and the like. However, as noted, it is preferable that the monomers used are methacrylate or acrylate esters, such as methyl methacrylate, and acrylamide monomers.

Given the crosslinking efficiency of 1',6,6'-trimethacryloyl-2,3,3',4,4'-penta-O-methylsucrose, this crosslinking agent may be used in smaller concentrations than conventional crosslinking agents. The amount of the crosslinking agent utilized will comprise those amounts which result in polymer having the desired degree of crosslinking. Typically, the amount of the crosslinking agent utilized will range from 0.01 to 50 mole percent, and more preferably, from 0.1 to 10 mole percent. However, of course, the amounts may be varied dependent upon the particular monomer and the desired properties of the resultant polymers.

The polymerizable mixture of the crosslinking agent and the monomer will preferably contain a free radical initiator, which can be a thermal initiator, photo initiator, chemical initiator, or a catalyst to initiate polymerization. However, an initiator or catalyst is not required since polymerization can also be induced by thermal means or by radiation.

The particular initiator or catalyst selected will depend upon the conditions at which the polymerization is to be effected and the desired properties of the resultant polymers. Suitable initiators and catalysts for polymerization processes are well known to those skilled in the art. Such initiators include, for example, alkoxy alkyl benzophenones acyl peroxides and are butyronitriles. This list is intended to be exemplary and other known initiators are within the scope of the present invention.

The actual amount of the initiator or catalyst utilized will typically range from 0.01 to 5% by weight, and preferably from 0.1 to 3% by weight. However, these amounts will vary dependent upon the particular initiator or catalyst selected, and the conditions of polymerization.

Methods for producing crosslinked polymers by the reaction of a monomer and a crosslinking monomer are well known to those skilled in the art. In the present invention, the particular polymerization conditions will vary dependent upon factors including, e.g., the particular monomer which is reacted with the 1',6,6'-trimethacryloyl-2,3,3',4,4'-penta-O-methylsucrose, the relative proportions thereof, the degree of crosslinking desired, the desired molecular weight of the polymer, whether polymerization is effected in bulk or in solution, the particular solvent, the presence of a free radical initiator, and the amount thereof, among other factors. The determination of suitable conditions for polymerization is within the level of skill in the art.

In order to further illustrate the present invention and the advantages thereof, the specific example is given, it being understood that the same is intended only as illustrative and in nowise limitative.

EXAMPLE

In order to establish the enhanced efficiency of the crosslinked polymers produced using 1',6,6'-trimethacryloyl-2,3,3',4,4'-penta-O-methylsucrose, the present inventors compared the swelling of crosslinked polymers produced using 1',6,6'-trimethacryloyl-2,3,3',4,4'-penta-O-methylsucrose when compared to trimethylpropane trimethacrylate, a conventional crosslinking agent.

A less efficiently crosslinked polymer has longer polymeric chains between crosslinks. Longer chains can stretch more easily than short chains. Consequently, this enables more solvent to diffuse in and the polymer swells more. In contrast, a more efficiently crosslinked polymer has shorter polymeric chains between crosslinks. Therefore, the polymer chains stretch less easily. Accordingly, fewer solvent molecules can diffuse in and the polymer swells less.

Therefore, as a means of establishing the greater crosslinking efficiency of 1',6,6'-trimethacryloyl-2,3,3',4,4'-penta-O-methylsucrose versus trimethylpropane trimethacrylate, a comparison was made of the weight of polymer samples prepared using identical mole ratios of the respective crosslinking agents before and after swelling in various solvents. Specifically, the ratio of the weight of the respective polymer samples before swelling (which weight will be designated $W_o$ herein) versus the weight of the polymer sample after swelling (which weight will be designated $W_s$ herein) will be determined.

It is well known in the art that if a linear polymer is soluble in a particular solvent, then the equivalent crosslinked polymer will swell in a solvent which dissolves the linear parent. Thus, it is important to select swelling solvents which are close to the solubility parameter of polymethyl methacrylate. Chloroform, 1,1,2,2-tetrachloroethane and 1,1,2-trichloroethylene were selected since their solubility parameters are close to that of polymethyl methacrylate; i.e., $$11.5 +/- 1 \left[\frac{cal}{cc}\right]^{\frac{1}{2}}.$$

The $W_s/W_o$ values were compared using trimethylpropane trimethacrylate (TMPTMAc) and 1',6,6'-trimethacryloyl-2,3,3',4,4'-penta-O-methylsucrose [(MAC)$_3$(OMe)$_5$sucrose] as crosslinking agents in solution. This procedure involved preparing copolymers by mixing methyl methacrylate monomer, the particular crosslinking agent and 2,2-azobisisobutyronitrile (as the free radical initiator) with a volume of chlorobenzene approximately equal to the total volume of methyl methacrylate monomer.

When effecting the swelling comparisons, variable amounts of the crosslinking agent of the present invention and the comparative crosslinking agent were combined with a fixed amount of the initiator, azobisisobutyronitrile (AIBN) and the chlorobenzene solvent.

For example, to obtain a 1.00 mole percent concentration of trimethylpropane trimethacrylate (TMPTMAc), 169.2 mg of TMPTMAc were mixed with 4.96 g (5.30 ml) of methyl methacrylate, 25 mg of AIBN and 5.30 ml of chlorobenzene.

To obtain a 0.75 mole percent concentration of TMPTMAc, 126.9 mg of TMPTMAc were mixed with 4.96 g (5.30 ml) of methylmethacrylate, 25 mg of AIBN and 5.30 ml of chlorobenzene.

To obtain a 0.50 mole percent concentration of TMPTMAc, 84.6 mg of TMPTMAc were mixed with 25 mg of AIBN, 5.30 ml of chlorobenzene and 4.98 g (5.32 ml) of methyl methacrylate.

Finally, to obtain a 0.25 mole percent concentration of TMPTMAc, 42.3 mg of TMPTMAc were combined with 25 mg of AIBN, 5.30 ml of cholorobenzene and 5.00 g (5.34 ml) of methyl methacrylate. Polymer samples containing identical mole percent concentrations of 1',6,6'-trimethacryloyl-2,3,3',4,4'-penta-O-methylsucrose were also prepared.

Specifically, to obtain a 1.00 mole percent concentration, 308 mg of 1',6,6'-trimethacryloyl-2,3,3',4,4'-penta-O-methylsucrose was mixed with 4.96 g (5.30 ml) of methyl methacrylate, 25 mg of AIBN and 5.30 ml of chlorobenzene.

To obtain a 0.75 mole percent concentration, 231 mg of 1',6,6'-trimethacryloyl-2,3,3',4,4'-penta-O-methylsucrose were mixed with 4.96 g (5.30 ml) of methyl methacrylate, 25 mg of AIBN and 5.30 ml of chlorobenzene.

To obtain a 0.50 percent concentration, 154 mg of 1',6,6'-trimethacryloyl-2,3,3',4,4'-penta-O-methylsucrose were combined with 4.98 g (5.32 ml) of methyl methacrylate, 25 mg of AIBN and 5.30 ml of chlorobenzene.

Finally, to obtain a 0.25 mole percent concentration, 77 mg of 1',6,6'-trimethacryloyl-2,3,3',4,4'-penta-O-methylsucrose were mixed with 5.00 g (5.34 ml) of methyl methacrylate, 25 mg of AIBN and 5.30 ml of chlorobenzene. Each of the resultant 10.6 ml polymer mixtures obtained was added to eight ml individual aliquots and used to fill up to the 30 cm mark in a polymerization tube which tube is 50 cm in length, 0.5 cm in diameter, and has a 2 mm wall thickness.

The mixtures were then degassed and the polymerization tubes sealed in vacuo using standard techniques. Each sample was then polymerized for the following times and temperatures: 25° C., 2 days; 35° C., 2 days; 45° C., 1 day; 55° C., 1 day; 65° C., 1 day; and 70° C., 1 day.

The samples were then removed from the polymerization tubes, rapidly cut into 1 cm cylinders and stored in air tight amber glass bottles. The volumes of the 1 cm long cylinders were then ascertained. The cylinders were then weighed to determine $W_o$, the weight of the polymer before swelling.

These cylinders were then soaked in chloroform for about 6 to 10 days until equilibrium swelling was reached. The polymer cylinders were then individually weighed so as to determine $W_s$, the swelling weight of the polymer. The swelling results are set forth in Table I below:

TABLE I

| Concentration in mole % of crosslinker | $W_s/W_o$ TMPTMAc | $W_s/W_o$ (MAc)$_3$ (OMe)$_5$ sucrose |
|---|---|---|
| 1.0 | 4.178 | 3.519 |
| 0.75 | 4.574 | 4.324 |
| 0.50 | 5.485 | 5.104 |
| 0.25 | 6.601 | 6.579 |

The identical swelling studies described above were effected except that 1,1,2,2-tetrachloroethane was utilized as the swelling solvent. Similarly, the 1 cm long polymer cylinders obtained were weighed to determine respective $W_o$ values (pre-swelling weights).

After these measurements were effected, the polymer cylinders were then swollen in 1,1,2,2-tetrachloroethane for about 6 to 10 days until equilibrium swelling was attained. The respective cylinders were then weighed to ascertain $W_s$ values (swelling weights). The results wherein 1,1,2,2-tetrachloroethane was the swelling solvent are set forth in Table II below:

TABLE II

| Concentration in mole % of crosslinker | $W_s/W_o$ TMPTMAc | $W_s/W_o$ (MAc)$_3$ (OMe)$_5$ sucrose |
|---|---|---|
| 1.0 | 4.725 | 3.906 |
| 0.75 | 4.818 | 4.817 |
| 0.50 | 6.170 | 5.512 |
| 0.25 | 7.576 | 7.143 |

A final comparison was made using 1,1,2-trichloroethylene as the swelling solvent. The eight polymer cylinders were otherwise identically prepared as described above.

Similarly, the weight of the eight 1 cm polymer cylinders was ascertained prior to swelling to determine the $W_o$ values. The respective cylinders were then soaked in 1,1,2-trichloroethylene for about 6 to 10 days until equilibrium swelling was attained. The individual polymer cylinders were then weighed to determine $W_s$, the weight of polymer after swelling, for each cylinder. The results are set forth in Table III below:

TABLE III

| Concentration in mole % of crosslinker | $W_s/W_o$ TMPTMAc | $W_s/W_o$ (MAc)$_3$ (OMe)$_5$ sucrose |
|---|---|---|
| 1.0 | 3.459 | 3.130 |
| 0.75 | 3.529 | 3.382 |
| 0.50 | 4.238 | 4.011 |
| 0.25 | 5.374 | 5.106 |

It can be clearly seen that copolymers prepared using 1',6,6'-trimethacryloyl-2,3,3',4,4'-penta-O-methylsucrose are consistently less swollen than the polymers prepared using trimethylpropane trimethylacrylate. Thus, the swelling studies provide clear evidence of the greater efficiency of 1',6,6'-trimethacryloyl-2,3,3',4,4'-penta-O-methylsucrose as a crosslinking agent when compared with trimethylpropane trimethacrylate, a conventional crosslinking agent, under equivalent conditions.

As noted, the swelling studies provide clear evidence of the relative high efficiency of 1',6,6'-trimethacryloyl-2,3,3',4,4'-penta-O-methylsucrose as a crosslinking agent. However, in order to further establish the relative efficiency of the two crosslinking agents, the present inventors effected the following additional comparisons.

Specifically, in order to evaluate the relative efficiency of the two crosslinking agents, the average molecular weight in the growing methyl methacrylate chains was established and compared to the average molecular weight between crosslinks ($\overline{M}_c$) as a function of the concentration of the particular crosslinking agent utilized to make the polymer. This may be established by various methods.

However, in the present invention, the value of ($\overline{M}_c$) was determined using the following formula which corresponds to the Flory-Huggins Theory. The formula is set forth below:[1]

[1] P. J. Flory, Principles of Polymer Chemistry, Cornell University Press, Ithaca, N.Y., 1953, p. 458–464 and 576–584 and from P. J. Flory, J. Chemical Physics, 1950, 18(1), p. 108.

$$\overline{M}_c = \frac{\text{molecular weight of monomer}}{[\text{efficiency of crosslinker}][\text{moles of crosslinker}][F] + [\text{moles of entanglements within the crosslinked polymer}]}$$

(wherein F is the effective functionality of the crosslinking agent).

The reciprocal of the equation above provides an equation for a straight line when $1/\overline{M}_c$ is plotted as a function of the concentration of the crosslinking agent.

$$\frac{1}{\overline{M}_c} = \frac{[\text{efficiency}][\text{moles crosslinker}][F] + [\text{moles entanglements}]}{\text{molecular weight of monomer}}$$

The slope of such a line denotes the efficiency of the crosslinking agent and the y-intercept illustrates the moles of entanglements present in the swollen mass when the concentration of the crosslinker approaches zero.

Using the Flory-Huggins Theory and concepts in equilibrium thermodynamics, the average molecular weight between crosslinks ($\overline{M}_c$) may be calculated using the experimental data from the equilibrium swelling studies set forth in Tables I–III above.

In the present invention, basic equation for $\overline{M}_c$ was slightly modified to account for the swelling which is expressed in terms of the equilibrium volume fraction of the polymer. As modified, $\overline{M}_c$ is represented by the following formula:

$$\overline{M}_c = \frac{V_m P_2 \left( \sqrt[3]{V_{2m}} - \frac{V_{2m}}{2} \right)}{-[\ln(1 - V_{2m}) + V_{2m} + X_{1,2} V_{2m}^2]}$$

wherein:

$$V_{equilibrium} = \frac{W_o}{P_2} + \frac{W_s - W_o}{P_1}$$

$$V_{2m} = \frac{W_o}{V_{equilibrium} P_2}$$

$$V_m = \text{molar volume of solvent} = \frac{\text{molecular weight of solvent}}{\text{solvent density}}$$

and
$P_2$ = polymer density
$P_1$ = solvent density
$W_o$ = initial weight of polymer sample (may contain solvent)
$W_s$ = weight of polymer sample after swelling
$V_{2m}$ = equilibrium volume fraction of polymer
$X_{1,2}$ = Flory-Huggins interaction parameter Table IV, set forth below, illustrates the calculated average molecular weights between crosslinks $\overline{M}_c$ as a function of the concentration of trimethylolpropane trimethacrylate in methyl methacrylate copolymers swollen in chloroform, 1,1,2,2-tetrachloroethane and 1,1,2-trichloroethylene.

TABLE IV

| Concentration in mole % of TMPTMAc | Chloroform $\overline{M}_e$ from $\frac{W_s}{W_o}$ | 1,1,2,2-Tetrachlorothane $\overline{M}_e$ from $\frac{W_s}{W_o}$ | 1,1,2-Trichloroethylene $\overline{M}_e$ from $\frac{W_s}{W_o}$ |
|---|---|---|---|
| 1.0 | 6,165 | 5,478 | 4,695 |
| 0.75 | 8,234 | 5,750 | 5,034 |
| 0.50 | 14,751 | 10,444 | 9,633 |
| 0.25 | 26,947 | 16,813 | 23,245 |

The calculated average molecular weights between crosslinks, $\overline{M}_c$ were also determined as a function of concentration for 1',6,6'-trimethacryloyl-2,3,3',4,4'-penta-O-methylsucrose in methyl methacrylate copolymers swollen in chloroform, 1,1,2,2,tetrachloroethane and 1,1,2-trichloroethylene. The results are listed below in Table V.

TABLE V

| Concentration in mole % of 1',6,6'-trimethacryloyl-2,3,3',4,4'-penta-O-methylsucrose | Chloroform $\overline{M}_e$ from $\frac{W_s}{W_o}$ | 1,1,2,2-Tetrachlorothane $\overline{M}_e$ from $\frac{W_s}{W_o}$ | 1,1,2-Trichloroethylene $\overline{M}_e$ from $\frac{W_s}{W_o}$ |
|---|---|---|---|
| 1.0 | 3,560 | 3,388 | 3,311 |
| 0.75 | 6,878 | 5,745 | 4,340 |
| 0.50 | 11,700 | 7,981 | 7,905 |
| 0.25 | 26,650 | 14,692 | 19,107 |

A comparison of the molecular weights between crosslinks for the methyl methacrylate copolymers containing trimethylolpropane trimethacrylate and 1',6,6'-trimethacryloyl-2,3,3',4,4'-penta-O-methylsucrose clearly illustrates that the copolymers prepared with the crosslinking agent of the present invention have smaller molecular weight values for the average molecular weights between crosslinks for the same given concentration of crosslinking agent, as indicated by Tables IV and V. Therefore, this provides further evidence that the crosslinking agent of the present invention comprises greater relative crosslinking efficiency than a comparative crosslinking agent under equivalent conditions.

Yet another comparison was made of the crosslinking efficiencies by ratio of the slopes when 1/Mc is plotted versus the moles of crosslinker from the $W_s/W_o$ data for each swelling solvent. The results are set forth in Table VI below:

TABLE VI

| | Tetrachloroethane | Chloroform | Trichloroethylene |
|---|---|---|---|
| W/W₀ Data slope 1',6,6'-trimethylacryloyl-2,3,3',4,4'-penta-O-methylsucrose slope trimethylolpropane trimethacrylate | 1.63 | 1.84 | 1.41 |

This data indicates that 1',6,6'-trimethacyloyl-2,3,3',4,4'-penta-O-methylsucrose comprises between 1.5 to 2.0 greater crosslinking efficiency than trimethylolpropane trimethacrylate under equivalent conditions.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for producing a composition including a crosslinked polymer which comprises polymerizing a mixture containing at least:
   (i) 1',6,6'-trimethacryloyl-2,3,3',4,4'-penta-O-methylsucrose monomer, and
   (ii) a monomer which is capable of being crosslinked by said 1',6,6'-trimethacryloyl-2,3,3',4,4'-penta-O-methylsucrose monomer,
   in amounts sufficient to produce a crosslinked polymer containing composition.

2. The method of claim 1, wherein the monomer capable of being crosslinked by 1',6,6'-trimethacryloyl-2,3,3',4,4'-penta-O-methylsucrose is selected from methacrylate ester monomers, acrylate ester monomers and acrylamide monomers.

3. The method of claim 2, wherein the methacrylate ester monomer is methyl methacrylate.

4. The method of claim 1, wherein the polymerization mixture further comprises a free radical initiator.

5. The method of claim 4, wherein the free radical initiator is 2,2'-azobisisobutyronitrile.

6. A polymerizable mixture suitable for the preparation of a crosslinked polymer which comprises at least:
   (i) 1',6,6'-trimethacryloyl-2,3,3',4,4'-penta-O-methylsucrose monomer, and (ii) a monomer which is capable of being crosslinked by said 1',6,6'-trimethacryloyl-2,3,3',4,4'-penta-O-methylsucrose monomer, in amounts sufficient for the production of a crosslinked polymer.

7. The polymerizable mixture of claim 6, wherein the monomer which is capable of being crosslinked by said 1',6,6'-trimethacryloyl-2,3,3',4,4'-penta-O-methylsucrose monomer is selected from methacrylate ester monomers, acrylate ester monomers and acrylamide monomers.

8. The polymerizable mixture of claim 7, wherein the methacrylate ester monomer is methyl methacrylate.

9. The polymerizable mixture of claim 6, wherein the mixture further comprises a free radical initiator.

10. The polymerizable mixture of claim 9, wherein the free radical initiator is 2,2'-azobisisobutyronitrile.

* * * * *